United States Patent
Lehikoinen et al.

(10) Patent No.: US 10,261,039 B2
(45) Date of Patent: Apr. 16, 2019

(54) METHOD AND APPARATUS FOR INVESTIGATING PERMITTIVITY IN A TARGET DOMAIN

(71) Applicant: ROCSOLE LTD, Kuopio (FI)

(72) Inventors: Anssi Lehikoinen, Kuopio (FI); Arto Voutilainen, Kuopio (FI)

(73) Assignee: ROCSOLE LTD, Kuopio (FI)

( * ) Notice: Subject to any disclaimer, the term of this patent is extended or adjusted under 35 U.S.C. 154(b) by 482 days.

(21) Appl. No.: 14/773,644

(22) PCT Filed: Mar. 7, 2013

(86) PCT No.: PCT/FI2013/050245
§ 371 (c)(1),
(2) Date: Sep. 8, 2015

(87) PCT Pub. No.: WO2014/135741
PCT Pub. Date: Sep. 12, 2014

(65) Prior Publication Data
US 2016/0025663 A1    Jan. 28, 2016

(51) Int. Cl.
*G01N 27/22* (2006.01)
*G01F 1/56* (2006.01)
(Continued)

(52) U.S. Cl.
CPC .......... *G01N 27/22* (2013.01); *G01N 17/008* (2013.01); *G01N 27/24* (2013.01)

(58) Field of Classification Search
CPC .. G01F 1/64; G01F 1/74; G01F 1/712; G01N 27/226; G01N 27/228
(Continued)

(56) References Cited

U.S. PATENT DOCUMENTS 5,005,402 A * 4/1991 Pischinger ............ G01N 27/07
123/1 A
5,807,251 A    9/1998 Wang et al.
(Continued)

FOREIGN PATENT DOCUMENTS

CN    2454777 Y    10/2001
CN    1854726 A    11/2006
(Continued)

OTHER PUBLICATIONS

Office Action issued by the State Intellectual Property Office of People's Republic of China in corresponding Chinese Patent Application No. 201380076432.4 dated Feb. 3, 2017 (22 pages including partial English translation).
(Continued)

*Primary Examiner* — Jonathan Han
(74) *Attorney, Agent, or Firm* — Buchanan, Ingersoll & Rooney PC

(57) ABSTRACT

A method for investigating permittivity within a target domain comprises a step of measuring, for a plurality of pairs of contact element groups, the contact elements of the contact element groups being arranged in capacitance measurement connection with the target domain, an electrical quantity of interest proportional to the capacitance of a capacitor formed by a pair of contact element groups; the contact elements comprising a plurality of electrodes supported between the target domain and an electrically conductive background body limiting the capacitance measurement zone of the electrodes. The contact elements may further comprise the electrically conductive background body.

16 Claims, 7 Drawing Sheets

(51) Int. Cl.
 *G01N 27/24* (2006.01)
 *G01N 17/00* (2006.01)
 *G06F 19/00* (2018.01)

(58) Field of Classification Search
 USPC .................. 324/663, 674; 702/65; 73/861.08
 See application file for complete search history.

(56) References Cited

U.S. PATENT DOCUMENTS

| | | | |
|---|---|---|---|
| 7,496,450 B2* | 2/2009 | Ortiz Aleman | G01F 1/64 702/6 |
| 2007/0186679 A1* | 8/2007 | Zangl | G01F 1/64 73/861.18 |
| 2009/0147616 A1* | 6/2009 | Leinonen | B01F 5/0471 366/142 |
| 2010/0332170 A1* | 12/2010 | Gao | G01N 27/228 702/65 |
| 2012/0048732 A1 | 3/2012 | Hayashi et al. | |
| 2013/0049770 A1* | 2/2013 | Basu | G01N 27/026 324/654 |
| 2013/0054191 A1 | 2/2013 | Kaipio et al. | |

FOREIGN PATENT DOCUMENTS

| | | |
|---|---|---|
| CN | 101241094 A | 8/2008 |
| CN | 102183575 A | 9/2011 |
| CN | 202256236 U | 5/2012 |
| WO | WO 95/24155 A1 | 9/1995 |
| WO | WO 2011/107657 A1 | 9/2011 |

OTHER PUBLICATIONS

International Search Report (PCT/ISA/210) dated Nov. 6, 2013, by the Finnish Patent Office as the International Searching Authority for International Application No. PCT/FI2013/050245.

Written Opinion (PCT/ISA/237) dated Nov. 6, 2013, by the Finnish Patent Office as the International Searching Authority for International Application No. PCT/FI2013/050245.

International Preliminary Report on Patentability (PCT/IPEA/409) dated Jun. 11, 2015 for International Application No. PCT/FI2013/050245.

Database WPI, Week 201245, Thomson Scientific, London, GB, XP-002766366, May 30, 2012.

Extended Search Report issued by the European Patent Office in corresponding European Patent Application No. 13877392.4 dated Feb. 6, 2017 (7 pages).

Two-phase Flow Electrical Capacitance Tomography, Chen Deyun, Full-text database of Chinese Excellent Doctoral Dissertation, Information Technology Series, vol. 1; pp. 1140-1134.

English Translation of Chinese Office Action dated Oct. 16, 2017 in corresponding Chinese Patent Application 2013800764324 (16 pages).

* cited by examiner

METHOD AND APPARATUS FOR INVESTIGATING PERMITTIVITY IN A TARGET DOMAIN

FIELD OF THE INVENTION

The present invention relates generally to methods and apparatuses for monitoring industrial processes by means of non-invasive monitoring techniques, in particular for investigating permittivity in such processes by means of external measurements of capacitances or some other capacitance-dependent electrical quantities of interest. Such techniques are often called electrical capacitance tomography ECT.

BACKGROUND OF THE INVENTION

Electrical capacitance tomography ECT is one specific field within the more general field of electrical tomography. ECT as such is a known technique allowing non-invasive monitoring of a target domain on the basis of determination of the permittivity within the target domain.

In general, ECT comprises providing a model of the target domain and the measurement arrangement, making capacitance-related measurements, and adjusting the mathematical model so as to reduce the differences between the simulated and the measured electrical quantity values until a sufficient consistency exist, after which the permittivity in the target domain is determined. Typically, this is implemented by generating an image of the permittivity distribution in the target domain. Permittivity, and in particular changes thereof provide information on the internal material properties and distributions within the target domain.

A typical example of utilization of ECT is imaging a multi-phase flow in an industrial process, wherein an image showing the areas or volumes of different phases within the material flow is generated. An example of this kind of method and different practical issues involved therein is discussed in U.S. Pat. No. 7,496,450 B2.

Recently, the inventors have found it being possible to use ECT also e.g. for monitoring scaling (fouling) of undesired deposit on, as well as possible wear of process equipment surfaces in various industrial processes.

Taking into account the basic principle of ECT lying on measuring capacitance or, more generally, some electrical quantity of interest proportional to capacitance, the measurement sensor design and the actual measurement setup plays an important role in reconstructing the permittivity within the target domain. Most commonly, an ECT sensor is implemented as a tubular body forming a part of the process pipe or vessel, the content of which is to be analyzed. The electrodes are arranged in an annular assembly along the tubular body wall. As is clear from the basic nature of a plate capacitor, the capacitance thereof being proportional to the size of the capacitor plates, the electrodes should be sufficiently large in order to ensure sufficiently strong signals. This is important, for example, to achieve a sufficient signal to noise ratio. On the other hand, the spatial resolution in reconstructing the permittivity distribution naturally deteriorates when the electrode size is increased. As a compromise, the circumference of the tubular sensor body is typically divided for 8 to 12 equally sized electrodes.

Given the compromised situation described above, it is clear that new solutions for improving the signals to be measured would be highly desired.

SUMMARY OF THE INVENTION

The purpose of the present invention is to provide an improved method, as well as an improved apparatus, for investigating permittivity in a target domain.

The present invention is characterized by what is presented in claims 1 and 9.

According to a first aspect, the present invention is focused on a method for investigating permittivity within a target domain. The target domain can be any two or three-dimensional domain within which the permittivity is to be determined. Typical examples are various industrial processes where liquid, gaseous and/or e.g. powdery materials are lead or stored in pipes, vessels or other types of containers.

The method comprises a step of measuring, for a plurality of pairs of contact element groups, the contact elements of the contact element groups being arranged in capacitance measurement connection with the target domain, an electrical quantity of interest proportional to the capacitance of a capacitor formed by a pair of contact element groups; the contact elements comprising a plurality of electrodes supported between the target domain and an electrically conductive background body limiting the capacitance measurement zone of the electrodes.

The general purpose of the step of measuring the electrical quantity of interest for a plurality of contact element groups is to provide measured data for determining the permittivity of the material(s) within the target domain. This determination can be based on, for example, comparing a mathematical model simulating the measurement and providing estimates for the electrical quantity of interest, and adjusting the model so as to decrease the differences between the simulated and the measured values of the electrical quantity of interest, until a desired consistency is achieved. As a result, the adjusted mathematical model provides information about the permittivity distribution within the target domain, which permittivity distribution, in turn, provides information on different materials present, and their distributions in the target domain. Typically, the permittivity distribution is presented as an image of the target domain. This general procedure of comparing a mathematical model and preparing an estimated reconstruction of the target domain permittivity is generally known as electrical capacitance tomography ECT.

In performing an ECT process as described above, the measurements of the electrical quantity of interest can be performed separately from the actual analysis, i.e. the inversion problem calculations and image reconstruction. In other words, the measurements, i.e. the measured results, may be just received as one step of such analysis. This allows, for example, an embodiment where the results of the measurements performed at a measuring site are sent electronically to an analysis site where the actual analysis is carried out. On the other hand, it is of course also possible and in the scope of the present invention to perform the measurements and analysis integrally, e.g. using a single analysis system comprising a sensor with the contact elements, appropriate measurement equipment, and computer means for performing the actual calculations.

The electrical quantity of interest can be any electrical quantity which is proportional to or dependent on the capacitance of a capacitor formed by a pair of contact element groups. The capacitance measurement connection between the contact elements and the target domain means that the contact elements are so connected to the target domain that capacitance measurements, or at least measurements of some characteristic electrical quantity proportional to the capacitance of capacitors formed by pairs of contact element groups, can be performed. To implement this, for example, there should not be any continuous electrically conductive body forming an equipotential shield between the contact elements and the target domain.

The capacitance or some other capacitance-dependent ("proportional to") electrical quantity as the electrical quantity of interest means that the method is primarily intended for investigating target domain comprising mainly electrically insulating materials. However, as is discussed later in this document, in some cases, also conductivity properties of the substances present in the target domain may be analyzed.

A "contact element group" means here one or more of the contact elements. Thus, a capacitor under observation in the method can be formed between just a pair of two contact elements, but one or both of such single contact elements can also be replaced by a group of at least two separate contact elements.

The electrodes comprised in the contact elements can be formed according to the known principles of implementing electrodes for capacitance measurements, particularly capacitance measurements for electrical capacitance tomography ECT. For example, the electrodes can be formed as electrically conductive plates arranged in an annular assembly mounted to the wall of a metallic or plastic pipe section acting as a support body for the electrodes. Alternatively, the electrodes may be formed e.g. as annular rings on a rod-like support body. These kinds of sensors and the details of the electrode configurations thereof are known in the art.

The measurement zone of the electrodes means the area or volume affecting the capacitances between the electrodes. The electrically conductive background body limits this area by forming an equipotential surface behind which the electrodes do not "see" in the capacitance measurements. In other words, when connecting a voltage between a pair of electrodes (or electrode groups), the electric field thereby generated does not extend behind the electrically conductive background body. Thus, the capacitance between the electrodes do not depend on the material(s) behind the conductive background body. Typically, the electrically conductive background body is a continuous body which is substantially bigger than the electrodes. For example, in known ECT sensors with a tubular geometry, such background body may be formed by an electrically conductive pipe forming the support body of the sensor, or, in the case of an electrically insulating pipe as the support body, an external tubular screen surrounding the insulating pipe.

According to the present invention, the contact elements of the plurality of pairs of contact element groups, for which the electrical quantity of interest is measured, further comprise the electrically conductive background body. In other words, the electrically conductive background body forms one of the contact elements used in the step of measuring, for a plurality of pairs of contact element groups, the electrical quantity of interest proportional to the capacitance of a capacitor formed by a pair of contact element groups. Thus, for at least one pair of contact element groups for which the electrical quantity of interest is measured, one of the contact element groups comprises the electrically conductive background body. The electrically conductive background body can form such contact element group alone or together with one or more of the electrodes.

Thus, the basic principle of the method is to use the electrically conductive background body as one additional "electrode", i.e. one contact element, via which the measurements are made. This basic principle provides great advantages over the prior art solutions. First, the electrically conductive background body as an additional contact element naturally provides more information on the target domain via the increased total number of possible measurements, and the new measurement geometries in those measurements where the electrically conductive background element is used. Further, the size of the background body is typically much larger than that of the electrodes, the measurement zone of which it limits. Thus, the capacitance of a pair of contact element groups where the electrically conductive background element forms one the contact elements is greater than that of the pairs formed by the electrodes only. The increased capacitance increases the measurement signal strength. This leads to many significant improvements.

First, sensitivity of the measurements to external disturbances and interferences is reduced when the signal level is increased. Naturally, the improved signal strength improves the signal to noise ratio. Both these effects mean that a simpler implementation of the measurement electronics is allowed, and the need for high-cost special electronic components is reduced. On the other hand, it may be possible in some applications to reduce the size of the actual electrodes, thereby improving the spatial resolution of determining the permittivity in the target domain. Further, the principle of the present invention may be implemented in the existing measurement systems with few device modifications only. This is due to the existence of an electrically conductive background body in all prior art sensor configurations. Thus, all what is required is to provide some connecting means allowing said use of the electrically conductive background body as one of the contact elements.

The actual measurements of the electrical quantity of interest can be performed according to the principles as such well known in the field of electrical capacitance measurements, particularly in the field of electrical capacitance tomography. As one preferred alternative, in the step of measuring the electrical quantity of interest, an alternating excitation voltage signal is supplied to one contact element group, and a response current signal is measured from another contact element group. The response current can be used as such as the electrical quantity of interest, or it may be used to calculate the actual capacitance. As the response current signal one can measure e.g. the amplitude and/or the phase of the current. The alternating excitation voltage signal can have, for example, a square, triangle, or saw-tooth wave form. If the response current signal to be measured is the phase of the response current, sinusoidal excitation voltage signal is preferred.

In the case of a tubular geometry of the sensor, also the electrically conductive background body comprises typically an electrically conductive tubular body. In prior art ECT sensors or measurement probes, such tubular body is commonly used to isolate the measurement zone affecting the capacitances between the pairs of the electrodes from the surroundings. In other words, such body acts as a screen, typically held at some constant potential during the measurements, to prevent the electrodes from "seeing" each other via the exterior of the intended measurement zone. The electrodes may be mounted to (however electrically insulated therefrom) such electrically conductive background body itself. This is the case in ECT sensors where the support body is in the form of an electrically conductive pipe section. On the other hand, the electrodes may be mounted to an electrically insulating tubular support body, in which case the electrically conductive tubular body is supported so as to cover the electrically insulating tubular body to which the electrodes are mounted. In other words, in this configuration, the electrically conductive tubular body forms an extra tubular jacket on the electrically insulating tubular body.

In both cases described above, electrically conductive tubular body may further comprise radially extending flanges or partition walls separating adjacent electrodes from each other so that they do not "see" each other directly in the tangential direction.

On the other hand, the tubular geometry of the sensor and the electrode assembly is only one possibility to implement the basic principles of the present invention. Instead of the tubular configuration, the electrically conductive background body may comprise an electrically conductive rod. In such case, the electrodes may be mounted on the surface of the rod (electrically insulated therefrom) e.g. as a series of ring-like electrodes encircling the arm of the rod. This kind of sensor configuration is suitable for investigating a cylinder-symmetric system where the three-dimensional inversion problem to be solved for reconstruction of the permittivity distribution needs to be solved in two directions only: the axial direction along the axis of the rod, and the radial direction.

As yet another example, the electrically conductive background body may comprise an electrically conductive plate-like body. In this kind of configuration, the electrodes can be located on the surface of the electrically conductive plate-like body. This kind of configuration may be implemented, for example, as a sensor to be inserted as a part of a wall of the vessel, the content of which is to be monitored.

Also in the case of a rod or a plate-like body as the electrically conductive background body, the electrodes may be mounted to a separate electrically insulating support body so that the electrically conductive background body lies behind this electrically insulating support body.

In general, in the case of an electrically insulating support body, the electrodes may be mounted on a surface of the support body, or may be partly or entirely embedded within it so that they are possibly not in direct contact with the exterior of the support body and/or the target domain.

In the above, the method of the present invention has been described as being focused on the actual measurement step only. However, it is also in the scope of the present invention to perform a more complete investigation method further comprising the steps of providing a mathematical model of the target domain determining the electrical quantity of interest for a plurality of pairs of contact element groups; adjusting the mathematical model so as to reduce the differences between the measured values of the electrical quantity of interest and those determined by the mathematical model; and determining the permittivity on the basis of the adjusted mathematical model. Thus, this embodiment of the present invention comprises a complete electrical capacitance tomography ECT process.

In general, the mathematical model defined above means a numerical representation of the relationships between the physical material properties of the two or three-dimensional target domain and the electrical quantity of interest. Thus, as stated above, the general purpose of the mathematical model is to provide estimates of the values of the electrical quantity of interest, which values are determined by the material properties in the target domain.

The primary electrical quantity affecting the capacitance is naturally the electrical permittivity in the target domain. In other words, the capacitance, and thus any electrical quantity of interest proportional to the capacitance of a capacitor formed between and by a pair of contact element groups, depend on the permittivity of the material(s) within the target domain. Conversely, in practice, the mathematical model preferably determines also the permittivity in the target domain. This can be perhaps determined as only one representative value, but more preferably as the permittivity distribution in target domain area or volume.

After having received the desired number of measurements of the electrical quantity interest, the mathematical model is adjusted so as to reduce the differences between the measured values of the electrical quantity of interest and those determined by the mathematical model. This means comparing the measured values of the electrical quantity of interest and the corresponding simulated values determined by the mathematical model, and changing the parameters of the mathematical model so that the simulated values becomes closer to the actual, measured ones.

When sufficient consistency between the measured and the simulated values of the electrical quantity of interest is achieved, the adjusted model representing the real target domain is used as a basis for determining the permittivity in the target domain.

For example, when the mathematical model determines the permittivity distribution in the target domain, the adjusted model provides information enabling reconstruction of the true permittivity distribution in the target domain. Such permittivity distribution and changes of the permittivity can be further used to determine, for example, the presence of different materials and/or phases in the target domain. In prior art, a typical example of utilization of ECT is imaging a multi-phase flow, wherein an image showing the areas or volumes of different phases within a material flow is generated. As another example, in one specific application of the present invention, the permittivity information can be used to monitor the presence of a solid scaling deposit formed on a surface of a pipe for leading a flowable material through the pipe. As yet another example, the determined permittivity can be used to evaluate the moisture present in a powdery material flowing or being stored in the target domain.

In practice, the comparison of the measured and the corresponding simulated values of the electrical quantity of interest, and changing the parameters of the mathematical is generally known as an inverse problem or inverse calculation. Solving an inversion problem is based on typically rather complex computational algorithms performed at least partly automatically by means of suitable computation programs installed in a suitable processor. Several different algorithms suitable for the present invention are known in the art. Because those algorithms are not in the core of the present invention, they are not discussed in more detail in this specification.

According to a device aspect, the principles of the present invention can also be implemented as an apparatus for investigating permittivity within a target domain, the apparatus comprising a sensor for measuring, for a plurality of pairs of contact element groups, the contact elements of the contact element groups being arranged in capacitance measurement connection with a target domain, an electrical quantity of interest proportional to the capacitance of a capacitor formed by a pair of contact element groups; the sensor comprising an electrically conductive background body and a plurality of electrodes supported so as to be located, when in use, between the target domain and the electrically conductive background body limiting the capacitance measurement zone of the electrodes, the electrodes being configured to serve as the contact elements.

The sensor and the details thereof, such as the electrodes, may be configured basically according to the principles known in the art in the field of capacitance measurements and, particularly, in the field of electrical capacitance tomography ECT.

According to the present invention, in addition to the electrodes, also the electrically conductive background body is configured to serve as one of the contact elements. In other words, the apparatus according to the present invention allows measuring the electrical quantity of interest by using the electrically conductive background body as one of the contact elements of the pair of contact element groups forming the capacitor. As described above in the context of the method aspect of the present invention, this provides great advantages via the increase signal level due to the larger size of the electrically conductive background body in comparison to the electrodes.

Being configured to serve as a contact element requires first that the electrically conductive background body is in capacitance measurement connection with the target domain. Thus, there should not be any continuous electrically conductive bodies or surfaces between the electrically conductive background body and the target domain. Also, the configuration of the electrically conductive background body must allow coupling of appropriate measuring equipment to the electrically conductive background body so that electric signals can be supplied to and/or received from it. For example, there may be connector means attached to the electrically conductive background body for coupling the electric signals to/from it. Such connector means may comprise, for example, one or more standard or specially designed cable connectors for connecting measurement cables to the electrically conductive background body. Moreover, also the overall shape and, in some cases, also the size of the electrically conductive background body may be specially designed for optimizing the measurements of the electrical quantity of interest using the electrically conductive background body as one of the contact elements. For example, the electrically conductive background body may comprise protrusions extending between the electrodes to serve as sub-screens preventing the adjacent electrodes from "seeing" each other directly but only via the target domain.

All what is stated and explained above about the advantages, details, and preferred features of the present invention in the context of the method aspect is applicable, mutatis mutandis, also to the apparatus according to the present invention. Thus, those issues are not repeated here, but some preferred embodiments are just summarized shortly below.

With regard to the actual type of measurements to be performed, in one preferred option, the sensor is configured to allow supplying an alternating excitation voltage signal to one contact element group, and a measuring a response current signal from another contact element group.

The electrically conductive background body may comprise an electrically conductive tubular body. This is a preferred choice, for example, for applications where the target domain to be monitored comprises an interior of a process pipe, and where the sensor is to be assembled as a part of the process pipe. The electrodes may be mounted directly (however, electrically insulated therefrom) to the conductive tubular body, which thus also forms a general support body of the sensor. This is a practical solution for applications where the process pipe is formed of a metal. The electrically conductive background body is then preferably formed of the same metal to ensure that the internal conditions within the pipe are the same at the location of the sensor and elsewhere in the pipeline.

Alternatively, the electrodes may be mounted to an electrically insulating tubular support body, the electrically conductive tubular body being supported so as to cover the insulating tubular support body. In this approach, there are thus two superposed tubular bodies, the electrically insulating one being the inner one. This approach is suitable for applications where the process pipe is formed of an electrically insulating material, wherein the electrically insulating tubular support body is preferably formed of the same electrically insulating material.

Instead of a tubular general geometry, the electrically conductive background body may also comprise an electrically conductive rod or an electrically conductive plate-like body.

Irrespective of the basic geometry and configuration of the conductive background body, the sensor is preferably configured so that when assembled as a part of a process equipment, e.g. as a part of a process pipeline in the case of a tubular sensor, the conductive background body is electrically insulated from the actual process equipment. This reduces coupling of disturbance signals to the measurements.

In the above, the apparatus according to the present invention is defined via the properties of the sensor only. The device aspect of the present invention can also be implemented as a more complete measurement system implemented as an apparatus comprising, in addition to such sensor, also at least one memory, and at least one processor coupled with the at least one memory; wherein the at least one memory comprises program code instructions, which when executed by the at least one processor, cause the apparatus to perform the following steps: providing a mathematical model of the target domain determining the electrical quantity of interest for a plurality of pairs of contact element groups; adjusting the mathematical model so as to reduce the differences between the measured values of the electrical quantity of interest and those determined by the mathematical model; and determining the location of the permittivity on the basis of the adjusted mathematical model.

The memories, processors, and program codes may be configured basically according to the principles known in the art in the field of electrical data processing and, particularly, in the field of electrical capacitance tomography ECT. For example, the at least one memory and the at least one processor may be implemented e.g. in the form of one or more computers, wherein suitable computer program code is installed for performing the method steps. In addition to the sensor and the at least one memory and processor, the apparatus may further comprise, for example, any equipment needed to perform the actual measurements. Naturally, such complete measurement system may also comprise any wirings and other connecting means for connecting the different parts of the system together so as to allow, for example, receipt of the measurement results by the at least memory and, on the other hand, control of the measurement equipment by the one or more computers.

BRIEF DESCRIPTION OF THE DRAWINGS

In the following, the present invention is described with reference to the accompanying drawings, wherein.

DETAILED DESCRIPTION OF THE EMBODIMENTS

Figure 1:
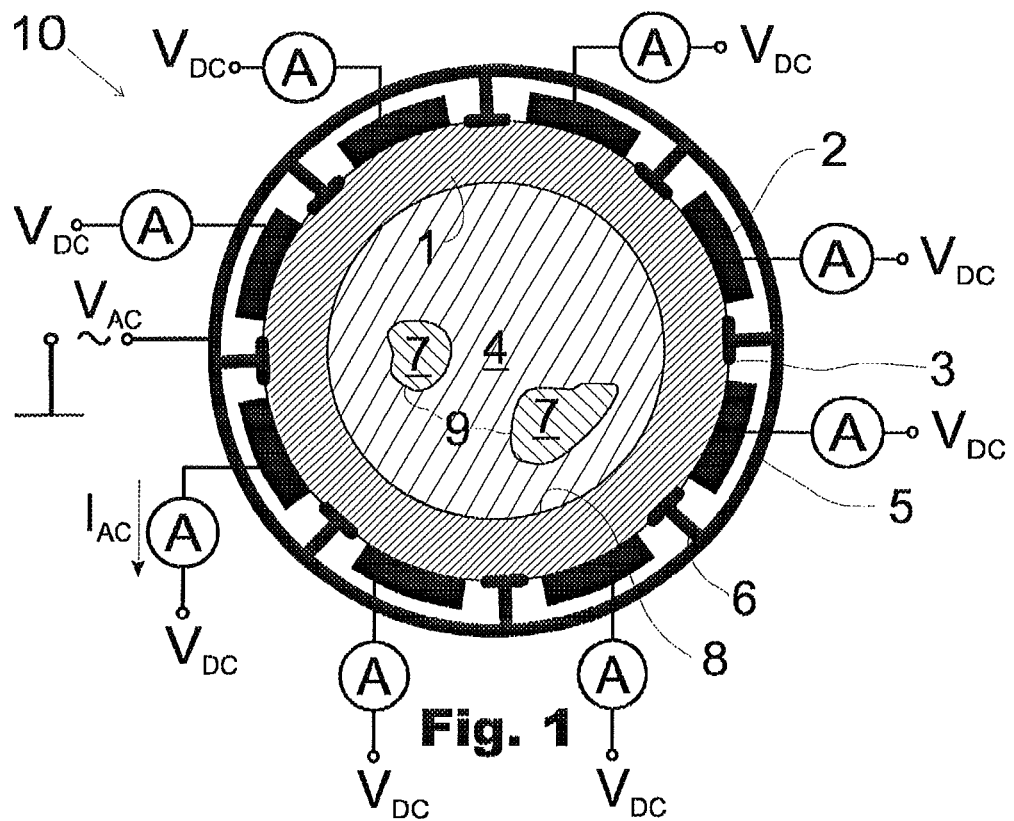
FIG. 1 shows a schematic cross-sectional view of a sensor having an electrically insulating support body with an electrode arrangement.

The sensor 10 of FIG. 1 comprises a section of an electrically insulating pipe 1 forming a support body, on the outer surface of which eight electrodes 2 are attached for performing measurements of one or more capacitance-dependent electrical quantities in a target domain 3 comprising the inner volume of the process pipe 1 as well as the pipe wall. Thus, in the example of FIG. 1, the boundary of the target domain 3 coincides with the outer surface of the pipe 1 and the inner surfaces of the electrodes 2 thereon. Alternatively, the electrodes could lie at least partly embedded in the pipe wall.

The electrically insulating pipe 1 is surrounded by a cylindrical (tubular) metal sheath 5, comprising flanges 6 extending radially from the sheath to the outer surface of the pipe 1. The metal sheath 5 serves as a screen to isolate the system of the electrodes and the target domain from its surroundings. Further, the flanges 6 extending between the electrodes prevent the adjacent electrodes from "seeing" each other directly via the exterior of the electrically insulating pipe. Thereby the measurement zone of the electrodes is limited to the electrically insulating pipe 1 and the inner volume thereof. In addition, the flanges 5 have transverse extensions at their ends on the outer surface of the pipe 1.

FIG. 1 illustrates a situation where the sensor is installed as a part of a process pipeline. The inner volume of the pipe 1 is filled with a liquid process material 4 flowing through the pipe. Clusters of a solid foreign substance 7 float along the liquid flow. By determining the permittivity in the target domain, it is possible to make conclusions on the materials present in the target domain, and thus determine the presence of different materials 4, 7 in the target domain and the interfaces 9 between such different materials. In another exemplary application, the permittivity information can be used to determine the humidity of a material in the target domain. Such material can be e.g. in the form of a powder, one specific example being milk powder.

Figure 2:
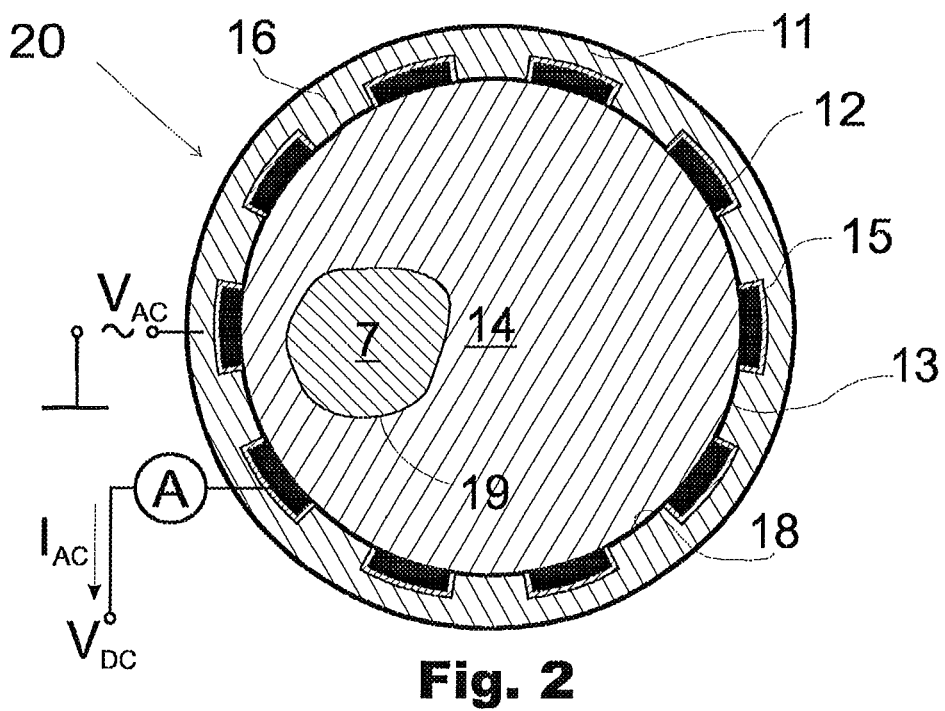
FIG. 2 shows a schematic cross-sectional view of a sensor having an electrically conductive support body with an electrode arrangement.

An alternative example of a sensor and measurement setup for investigating permittivity in a target domain is shown in FIG. 2. As an essential difference in comparison to FIG. 1, the sensor 20 of FIG. 2 comprises a section of an electrically conductive pipe 11 formed e.g. of some metal. In the point of view of measuring capacitance-dependent electrical quantity values, an electrically conductive pipe necessitates the electrodes 12 being in a direct contact with the pipe inner volume. In this kind of situation, the target domain 13 in which the measurements are to be made is limited by the electrodes and the electrically conductive pipe inner surface 18 itself. Further, due to the electrically conductive material of the pipe 11, each electrode is electrically insulated from the pipe by means of thin electrically insulating 15 layer located between the electrode and the pipe wall. The electrodes 12 are placed in cavities formed in the pipe inner surface so that between the electrodes, the pipe wall forms partition walls 16 isolating the adjacent electrodes so that they cannot "see" each other directly in capacitance measurements but only via the pipe inner volume.

Also in the situation illustrated in FIG. 2, there are clusters of a solid foreign substance 17 floating along the liquid process material 14 flowing through the pipe inner volume.

In FIGS. 1 and 2, eight and ten electrodes, respectively, have been installed on the pipes. However, these are just examples only, not limiting the applicability of the present invention to any number of electrodes suitably configured to allow measuring capacitances or other capacitance-dependent electrical quantities between the electrodes. Further, FIGS. 1 and 2 illustrate cross-sectional views of process pipes and one electrode ring only, thus referring to a two-dimensional target domain. However, it is possible to measure and monitor a three-dimensional target domain by arranging electrodes in several rings or layers along the axial direction of the process pipe.

For performing the actual measurements, the metal sheath 5 and the flanges 6 thereof in the sensor of FIG. 1, and the metal pipe 11 in the sensor of FIG. 2, are coupled to an alternating voltage $V_{AC}$ serving as an excitation signal. To allow this, there may be any appropriate connectors (not illustrated in FIGS. 1 and 2) attached to the metal sheath 5 and the metal pipe 11. Each of the electrodes 2, 12, in turn, is connected to a reference DC voltage $V_{DC}$ via a current measuring circuit (in FIG. 2, for the sake of clarity of the drawing, this is illustrated for one of the electrodes only). This measurement connection allows measurement of capacitances of the capacitors formed by the pairs of the electrically conductive metal sheath 5 or the metal pipe 11 and the electrodes 2, 12 indirectly via the current measurements. In other words, the capacitance of each capacitor can be calculated from the measured response current signal $I_{AC}$ when the excitation voltage signal is known.

Figure 6:
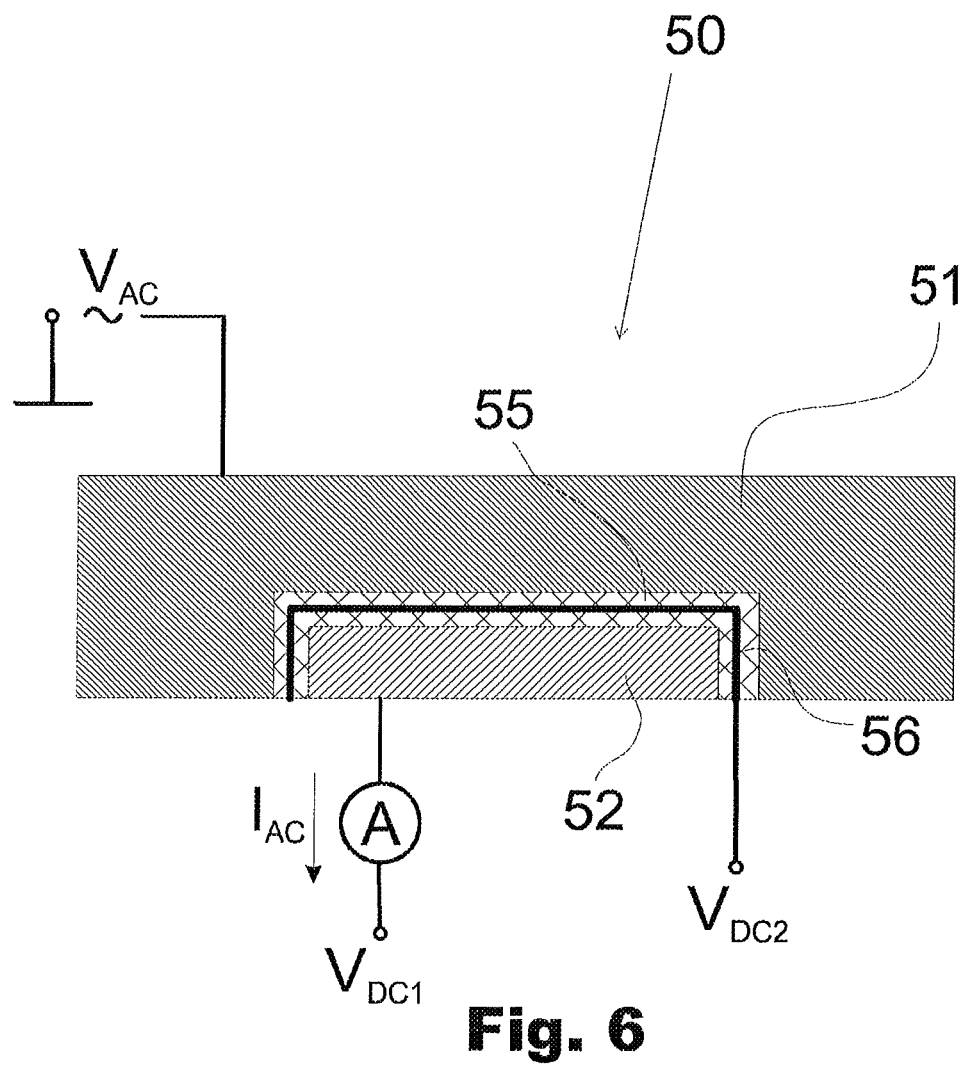
FIG. 6 shows a detailed view of a sensor configuration.

Though not illustrated in FIGS. 1 and 2, for the sake of clarity of the drawings, it is preferable to have additional conductive screens placed between the electrodes 2, 12 and the metal sheath 5 (FIG. 1) or the metal pipe 11 (FIG. 2). Such conductive screen forms an equipotential surface between the electrode and the metal sheath or the metal pipe, and prevents the electrode and the sheath/pipe to "see" each other directly via the region between them. The principle of such additional screen, applicable to any sensor configuration according to the present invention, is illustrated in FIG. 6.

Instead of the actual capacitance of a capacitor, it may be sufficient in some applications to determine some other electrical quantity of interest proportional to the capacitance, e.g. just the amplitude or the phase of the response current signal $I_{AC}$.

Capacitance, or some other electrical quantity of interest proportional to capacitance, is naturally dependent on the permittivity distribution within the target domain. Thus, the capacitance measurements provide information on this permittivity distribution which, in turn, as described above, can be used to make conclusions on the material conditions in the target domain.

In practice, the permittivity of a material is generally a complex valued quantity, thus having both a real and an imaginary portion. When observed in AC conditions, a complex permittivity of a material affects both the amplitude and the phase of the response current. Measuring only the amplitude of the current gives information on the real part of the permittivity only, whereas the phase information links the measurement to the complex portion of the permittivity. On the other hand, complex permittivity means that also the capacitance is a complex quantity. As an interesting issue, if both the phase and amplitude information of the supplied and measured signals are taken into consideration, also the electrical conductivity distribution within the target domain can possibly be estimated. When phase information is to be measured, sinusoidal supply voltage is preferably used.

In addition to measuring the electrical quantity of interest by using the metal sheath 5 or the metal pipe 11 as an excitation contact element and the electrodes 2 as response contact elements, the measurements can be repeated respectively for using each of the electrodes as the excitation contact element. As a general rule, if there are N contact elements (the electrically conductive background body plus N−1 electrodes) in the measurement system, N*(N−1)/2 independent capacitance values can be determined.

On the other hand, in the situations illustrated in FIGS. 1 and 2, the current measurements are performed for pairs of the electrically conductive background body and single electrodes only. Alternatively, the measurements can be performed for pairs of contact element groups where at least one of the excitation contact element group and the response contact element group comprises several contact elements. For example, a measurement can be performed for a capacitor formed between the background body and a group of several electrodes.

Figure 3:
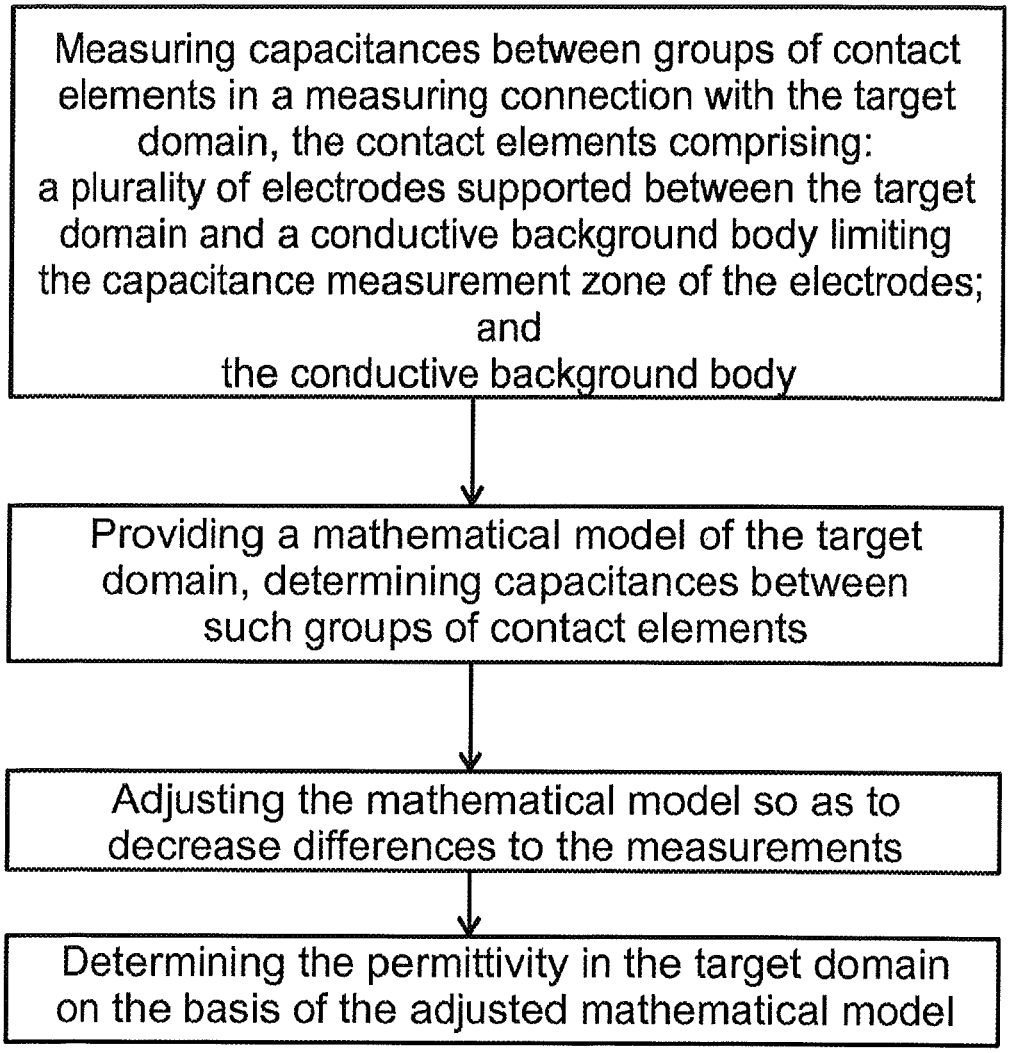
FIG. 3 is a flow chart illustration of a method for investigating permittivity in a target domain.

In the following, an example of a complete process for investigating the permittivity in the target domain by electrical capacitance tomography ECT, including also the computational steps, is explained by reference to the flow chart of FIG. 3.

First, capacitances between groups of contact elements in a measuring connection with the target domain are measured, using contact elements which comprise a plurality of electrodes, supported between the target domain and an electrically conductive background body limiting the capacitance measurement zone of the electrodes, and the electrically conductive background body itself. Thus, in at least one measurement, the electrically conductive background body is used as one of the contact elements forming the contact element groups. The measurements can be performed, for example, according to the principles described above with reference to FIGS. 1 and 2. Alternatively, any other known measurement arrangement suitable for providing measurements for an ECT process can be used.

As an important step of the ECT process, a mathematical model of the target domain is provided and stored e.g. in the memory of a computer. Mathematical model is built so as to comprise sufficient information to determine capacitances or some other capacitance-dependent electrical quantities between different electrode pairs or pairs of electrode groups. The information required for such determination can comprise e.g. the permittivity distribution within the target domain 3, 13. In practice, the model is a numerical representation of the physical target domain, the model including sufficient information about the material properties within the target domain so that estimates of the selected characteristic electrical quantity values to be measured by the electrodes can be determined on the basis of this information. The numerical model is divided into a plurality of discrete nodes or cells, each representing that particular location within the target domain.

When the required number of measurements and the mathematical model are available, the capacitances or other capacitance-dependent electrical quantity values determined by the mathematical model are compared with the measured results, and the model, i.e. its parameters, is adjusted so that the difference between the modelled and measured values is decreased. The goal is to find a permittivity distribution within the target domain for which the numerical model outcome corresponds closely to the measurements. In this comparison and adjustment, principles and algorithms as such known in the field of ECT and inversion mathematics can be used. For example, when generating a complete reconstruction of the permittivity distribution within the target domain, image reconstruction algorithms may generally be non-iterative or iterative algorithms. Among the first algorithm group, one simple and fast algorithm is the Linear Back-Projection (LBP) algorithm. In the LBP method, the relationship between the capacitance and permittivity distribution can be approximated in a linear normalized form as:

$$B = S \cdot X \quad (1)$$

where B is a normalized capacitance vector, S is a transducer sensitivity matrix (normalized capacitance with respect to normalized permittivity), and X is a normalized permittivity vector. The task in the analysis is to find out X, while B is known and S is predetermined as desired. Further information can be found e.g. in "Realization of linear back-projection algorithm for capacitance tomography using FPGA" by Almashary et al, 4th World Congress on Industrial Process Tomography, Aizu, Japan 2005.

The actual adjustment of the mathematical model may be based on a Bayesian inversion approach in which a statistical model is constructed for the effects due to the variations in geometry. In the following, this is discussed in more detail.

In general, the key step in the ECT image reconstruction comprises building a feasible numerical model of the system under inspection. The model gives the relations between the permittivity distribution and the mutual capacitances of the electrode configuration. With the aid of this model, the goal is to determine an estimate for the permittivity distribution so that the modeled capacitances are in close agreement with measured ones. In the Bayesian inversion approach the permittivity distribution and observed data are modeled as random variables, and the objective is to determine the probability density function of the permittivity distribution conditioned over the measurements. Measurements do not usually provide sufficient information so that a unique solution would exist; therefore, it is necessary to employ appropriate prior densities for the permittivity $\varepsilon(x)$.

Statistical properties of the measurement noise affect the quality of the reconstructed images, and with the Bayesian approach the statistics of the measurement noise can be modeled and accounted for in computations. The numerical model needed in the ECT imaging is an approximation of the actual behavior of the measurement system. At least the model suffers from inaccuracies due to numerical approximation of the governing continuous mathematical model. In addition, the system modeling may be challenging because the geometry is not usually perfectly known due to mechanical tolerances of the manufacturing. Furthermore, small changes in external measurement conditions (resulting e.g. to dimension changes due to thermal expansion) may lead to additional errors in the estimated permittivity distributions since their effects are not directly related to the used model. The effects of these types of modeling uncertainties can be, to some extent, compensated using an approximation error approach in which a statistical model is constructed for the effects of the model uncertainties using numerical simulations. Bayesian inversion approach is a natural framework for incorporating information on model errors into image reconstruction.

The goal in the Bayesian inversion is to determine the probability density function of the primal quantity conditioned over observations. In practical applications, it is usually necessary to determine some point estimates to give a concrete view of the situation on the ECT sensor. The computation of point estimates typically leads to optimization problems which are solved using the Newton's method or the Gauss-Newton method. Alternatively, another popular point estimate is the (conditional) expected value which is usually sought using sampling-based integration methods such as the Markov Chain Monte Carlo methods.

After adjusting the mathematical model so that a sufficient consistency between the measurements and the model exists, the permittivity is determined on the basis of the adjusted model.

Figure 4:
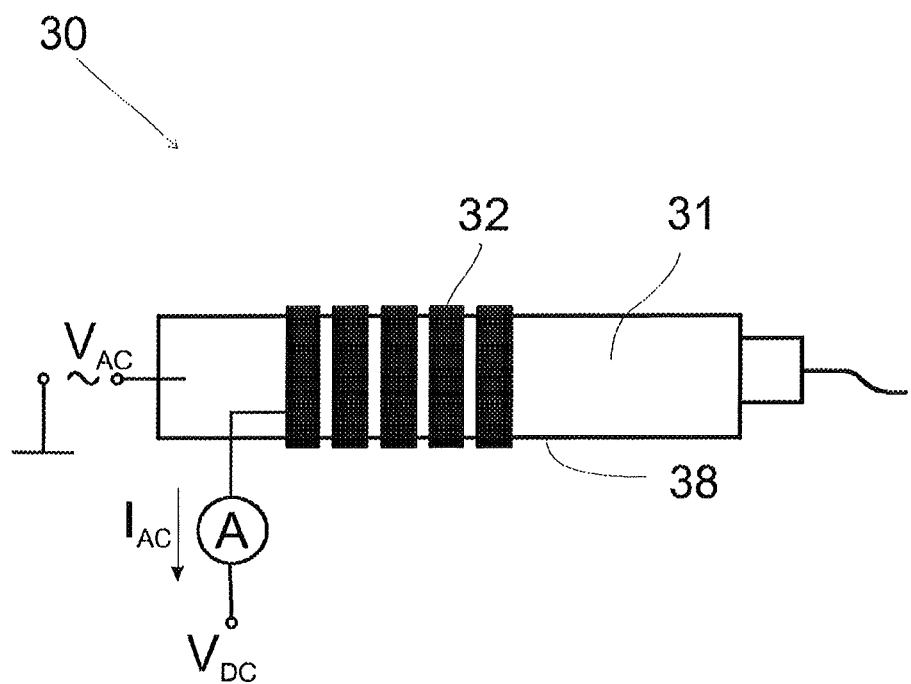
FIG. 4 shows a schematic side view of another type of sensor.

In some applications, it is possible to reduce the computational cost of the ECT process by taking advantage of symmetry. FIG. 4 shows a sensor 30 comprising an electrically conductive rod 31 forming a support body, and an electrode configuration wherein a plurality of ring electrodes 32 is mounted on the surface 38 of the rod-shaped support body. Potential fields generated by ring-like electrodes are cylinder-symmetric. Thus, a Finite Element Method (FEM) approximation used to model the target domain can be formulated in two dimensions (axial and radial) only, which reduces the computational complexity remarkably. Also in this example, the electrically conductive rod, forming an electrically conductive background body limiting the capacitance measurement zone of the electrodes 32, is configured to be used as one contact element in the measurements. In some applications, it may be required that the rod and the electrodes thereon are isolated from direct contact with the actual process environment. This isolation can be implemented e.g. by placing an electrically insulating hood on the rod and the electrodes thereon.

Figure 5:
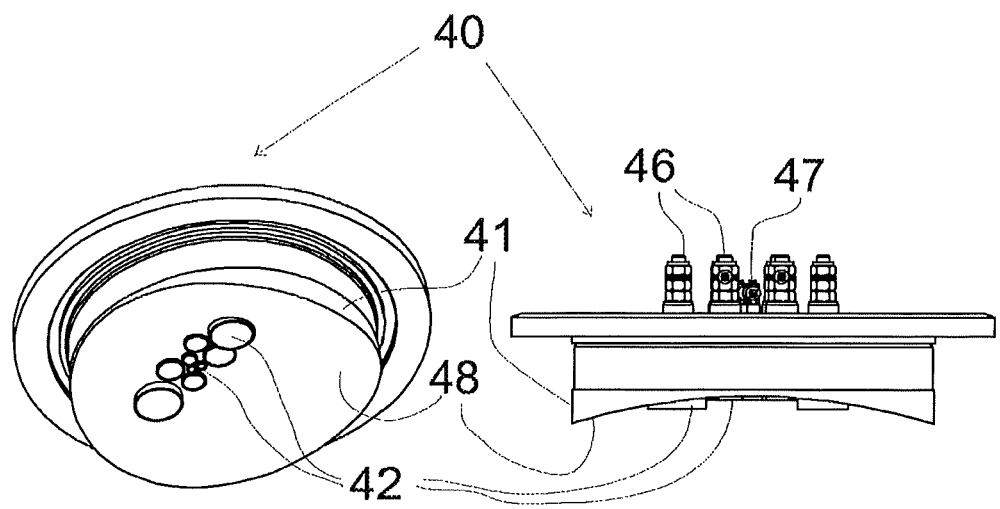
FIG. 5 shows yet another type of sensor.

As yet another alternative, the support body can be formed as a simple plate-like body 41, as is the case in the sensor 40 shown in FIG. 5. The exemplary sensor 40 of FIG. 5 is configured to be installed through a wall of a cylindrical vessel so that the actual support body 41, having a plurality of electrodes 42 thereon, faces towards the interior of the vessel. The backside of the sensor comprises a plurality of first connectors 46 and a second connector 47 for connecting the electrodes 42 and the plate-like body 41, respectively, to appropriate measurement equipment for using them as contact elements for capacitance measurements. In the example of FIG. 5, there are electrodes 42 with different sizes.

The surface 48 of the plate-like body is shaped curved so as to coincide with the inner surface of the wall of the cylindrical vessel. Naturally, the boundary surface of a plate-like support body could also be planar or have some other non-planar shape than the curved one shown in FIG. 5. Also, it is to be noted that the thickness of a "plate-like" support body can vary according to the conditions of the actual application at issue.

FIG. 6 shows a portion of an electrically conductive background body 51 forming a support body of a sensor 50. An electrode 52 is mounted in a recess formed in the electrically conductive background body. In addition to an electrically insulating layer 55, there is an additional electrically conductive screen 56 between the electrode 52 and the electrically conductive background body 51. The additional screen is connected to a second DC voltage $V_{DC2}$ which may be the same as the first DC voltage $V_{DC1}$ to which the electrode 52 is connected. Thus, from the point of capacitance measurements, the additional screen forms an equipotential surface between the electrode and the conductive background body. The purpose of the additional screen is to prevent direct coupling of measurement signals via the area between the electrically conductive background body 51 and the electrode 52. The basic principle of such additional electrically conductive screen is applicable to any geometry of the sensor. For example, it is preferably used in each of the sensors of FIGS. 1, 2, 4, 5, and FIG. 7 below.

Figure 7:
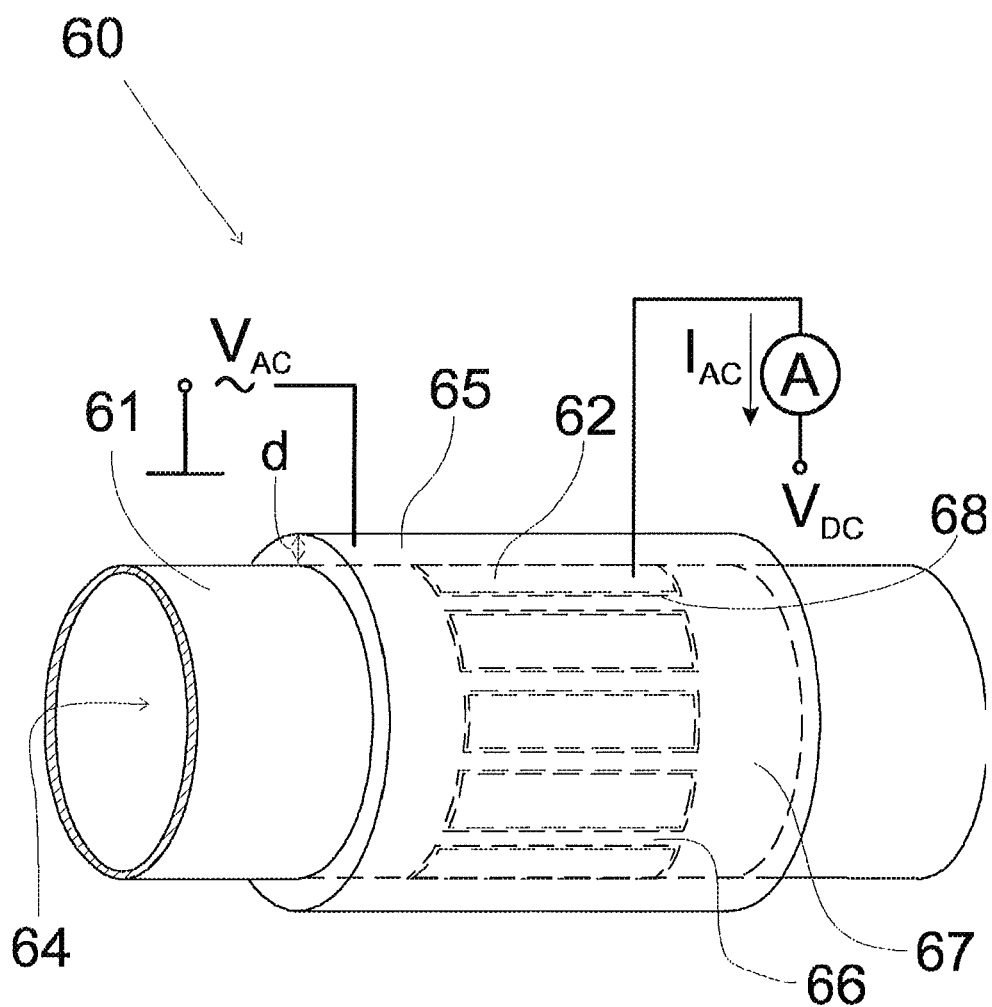
FIG. 7 shows a three-dimensional view of a sensor configuration.

FIG. 7 shows an insulating pipe section 61 serving as a support body for a sensor 60, wherein a plurality of electrodes 62 have been mounted in an annular assembly on the outer surface of the pipe. The electrodes 62 are longitudinal rectangular structures extending in the direction of the pipe longitudinal axis. The sensor further comprises a metallic sheath body 65 encircling the pipe and the electrode assembly thereon. The metal sheath body, having a thickness d, is mounted to the insulating pipe outer surface. It comprises recesses 68 for the electrodes 62 similarly to the configurations illustrated in FIGS. 2 and 6. Thus, between the electrodes, the sheath body comprises protrusions 66 extending to the level of the front surfaces of the electrodes similarly to the sensor illustrated in FIG. 2, thereby forming partition walls preventing the adjacent electrodes from "seeing" each other directly in capacitance measurements. The metal sheath body located behind the electrodes limits the measurement zone of the electrodes so that the electrodes do not "see" behind the sheath. In the longitudinal direction of the pipe, the metal sheath continues to a distance from the electrode assembly so as to limit the measurement area of the electrodes also in this longitudinal direction. Naturally, though not illustrated in the drawing of FIG. 7, the metal sheath 65 must be electrically insulated from the electrodes. Further, the electrodes and the sheath are preferably further isolated from each other by an additional screen placed between them according to the example of FIG. 6.

Although FIG. 6 shows a preferred sensor configuration, it is not absolutely necessary for the basic principles of the present invention to have the partition walls and/or the sheath directly on the outer surface of the insulating pipe. The sheath can lie at a distance from the insulating pipe similar to FIG. 1, and be even configured as a smooth structure without any protrusions/flanges for forming the partition walls. However, in such a case the target domain to be modeled is larger and, in addition, the contribution of the primary region of interest (i.e. the interior of the pipe) in the measured electrical quantity can be significantly lower than with the abovementioned sensor design.

Though in FIGS. 1, 2, 4, 6, and 7 measurement arrangements are illustrated wherein a voltage excitation signal is supplied to the conductive background body (conductive sheath, pipe, rod, plate, etc.) of the sensor, and response current signals are measured via the electrodes, it is clear that the basic principle of the present invention is not limited to this particular case only. Instead, the conductive background body and the electrodes can be used as the contact elements of the measurements in any arrangement and combination. Further, the signals are not limited to those excitation voltage and response current signals. The only necessary requirement according to the present invention is that also the conductive background body is used as one contact element via which the measurements are performed.

Figure 8:
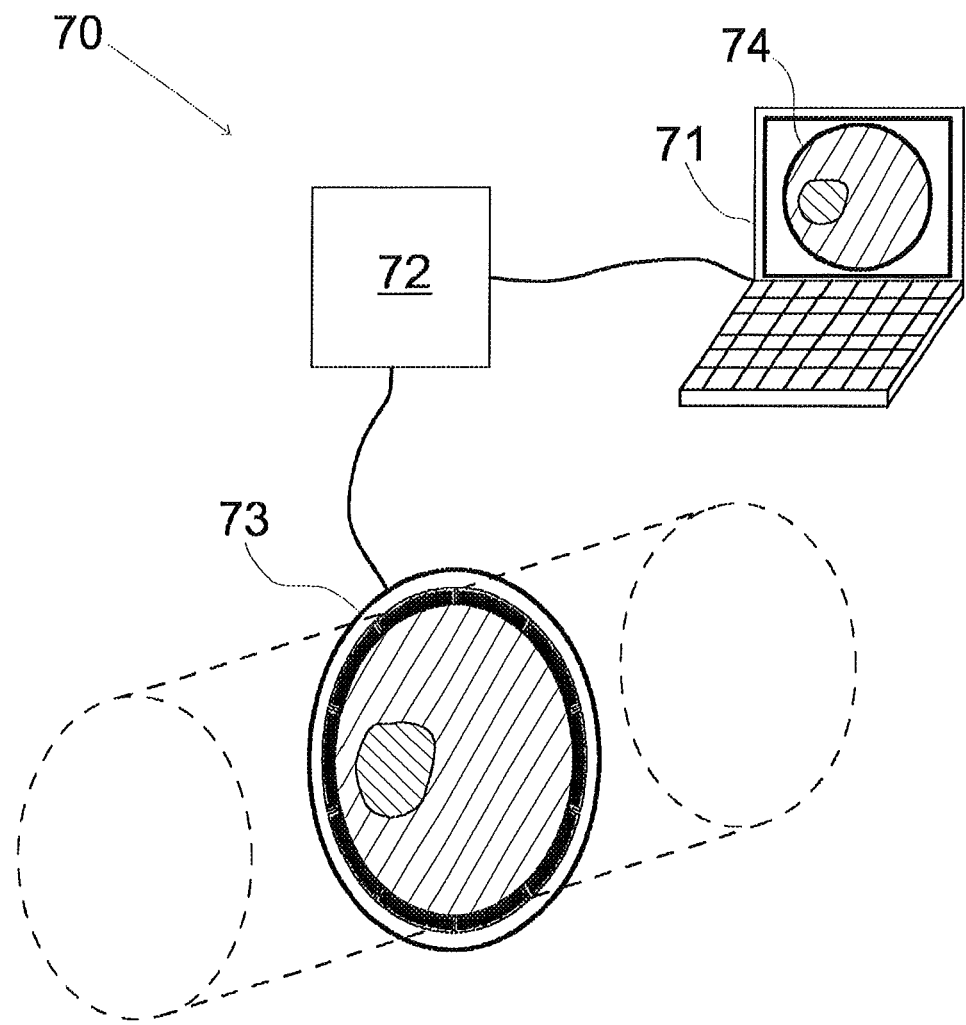
FIG. 8 shows an example of a complete system for determining permittivity in a target domain.

FIG. 8 illustrates schematically a system 70 by which the ECT process as described above can be carried out. In the operational core of system, there is a computer 71 comprising an appropriate number of memory circuits and processors for storing the mathematical model and performing the computational steps of the method. The system further comprises a measurement electronics unit 72 and a sensor 73 comprising an annular support body and a plurality of electrodes. The support body and the electrodes can be configured e.g. according to those illustrated in FIG. 2. The measurement electronics unit is connected to the computer so that the measurement electronics unit can be controlled by the computer and that the measurement results can be sent to and received by the computer for further processing. The computer comprises a program code configured to control the computer to carry out the steps of the method as described above. As a result of the method performed by the system, an image 74 of the target domain is generated on the basis of the reconstructed permittivity distribution within the target domain inside the annular support body of the sensor 73. The image shows the domain of different materials and the interfaces between them.

Figure 9:
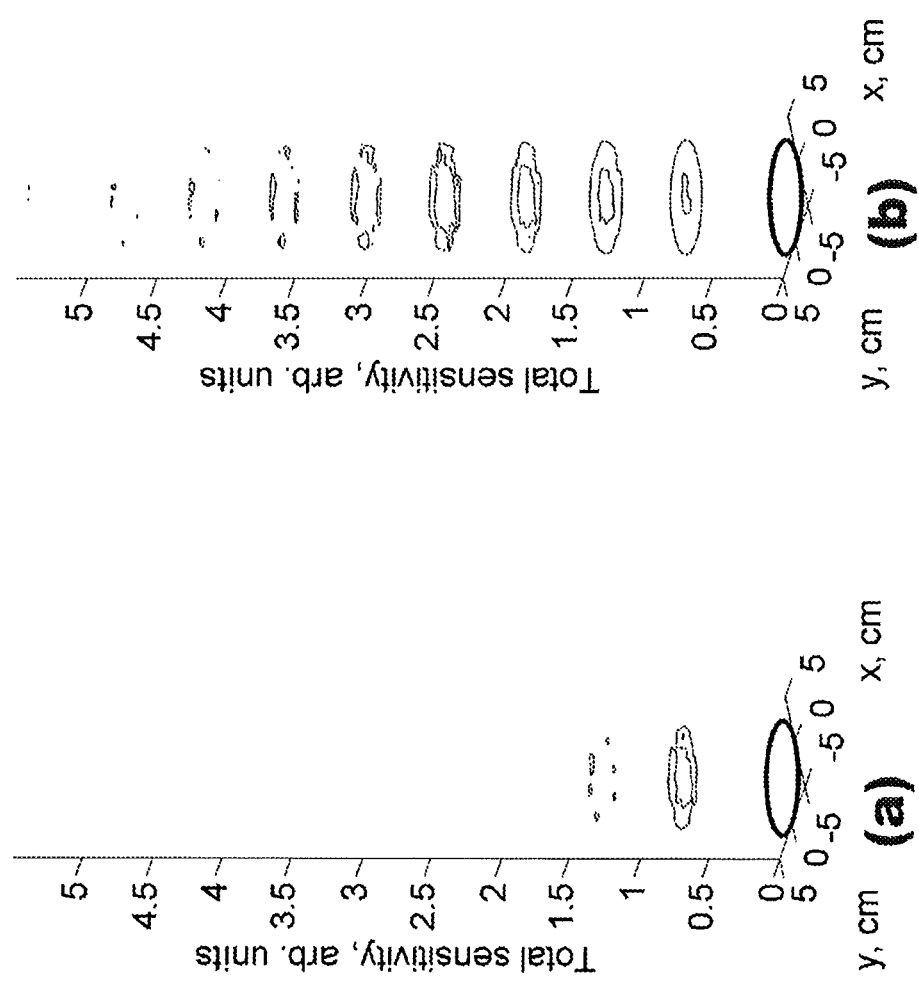
FIG. 9 shows an example of the sensitivity improvement provided by the present invention.

FIG. 9 shows the results of a sensitivity analysis in a case of a pipe sensor. A metal pipe with diameter of 10 cm was used as the basic geometry, and eight electrodes were mounted to the conductive pipe wall similarly as in FIG. 2. The electrodes were insulated from the pipe and additional screens illustrated in FIG. 6 were used in the region between the pipe and electrodes. In the simulation, an excitation voltage was supplied to one of the contact elements, and response currents were measured from each of the other contact elements. This was repeated until each of the contact elements had served as the supplying one. Sensitivity describes how much the observed signal changes due to unit change in the permittivity distribution in certain location. Sensitivities were analyzed for the conventional measurement case where only the electrodes were used for excitations and measurements, and for the case where, in addition, the pipe wall was used for excitation and current measurement. Graph (a) presents the average sensitivity (3D contour plot of sensitivity in arbitrary units) for the conventional approach where only the electrodes were used as the contact elements. Graph (b) shows the resulted sensitivity distribution when also the pipe wall was used as one of the contact elements. The graphs (a) and (b) clearly show the improved sensitivity of the analysis when also the electrically conductive background body is used as one of the contact elements in the measurements.

It is obvious to a person skilled in the art that with the advancement of technology, the basic idea of the invention may be implemented in various ways. The invention and its embodiments are thus not limited to the examples described above; instead they may freely vary within the scope of the claims.

The invention claimed is:

1. A method for investigating permittivity within a target domain, the method comprising:
measuring, for a plurality of pairs of contact element groups, the contact elements of the contact element groups being arranged in capacitance measurement connection with the target domain, an electrical quantity of interest proportional to the capacitance of a capacitor formed by a pair of contact element groups; and
determining one or more material properties of one or more materials within the target domain based on the measured electrical quantity;
the contact elements comprising a plurality of electrodes supported between the target domain and an electrically conductive background body limiting the capacitance measurement zone of the electrodes;
wherein the contact elements further comprise the electrically conductive background body.

2. A method as defined in claim 1, wherein in the step of measuring the electrical quantity of interest, an alternating excitation voltage signal ($V_{AC}$) is supplied to one contact element group, and a response current signal ($I_{AC}$) is measured from another contact element group.

3. A method as defined in claim 1, wherein the electrically conductive background body comprises an electrically conductive tubular body.

4. A method as defined in claim 3, wherein the electrodes are mounted to the electrically conductive tubular body.

5. A method as defined in claim 3, wherein the electrodes are mounted to an electrically insulating tubular support body, the electrically conductive tubular body being supported so as to cover the electrically insulating tubular support body.

6. A method as defined in claim 1, wherein the electrically conductive background body comprises an electrically conductive rod.

7. A method as defined in claim 1, wherein the electrically conductive background body comprises an electrically conductive plate-like body.

8. A method as defined in claim 1, wherein the method further comprises the steps of:
providing a mathematical model of the target domain determining the electrical quantity of interest for a plurality of pairs of contact element groups;
adjusting the mathematical model so as to reduce the differences between the measured values of the electrical quantity of interest and those determined by the mathematical model; and
determining the permittivity on the basis of the adjusted mathematical model.

9. An apparatus for investigating permittivity within a target domain, the apparatus comprising a sensor for measuring, for a plurality of pairs of contact element groups, the contact elements of the contact element groups being arranged in capacitance measurement connection with a target domain, an electrical quantity of interest proportional to the capacitance of a capacitor formed by a pair of contact element groups;
the sensor comprising an electrically conductive background body and a plurality of electrodes supported so as to be located, when in use, between the target domain and the electrically conductive background body limiting the capacitance measurement zone of the electrodes, the electrodes being configured to serve as the contact elements;
wherein the electrically conductive background body is configured to serve as one of the contact elements.

10. An apparatus as defined in claim 9, wherein the sensor is configured to allow supplying an alternating excitation voltage signal ($V_{AC}$) to one contact element group, and a measuring a response current signal ($I_{AC}$) from another contact element group.

11. An apparatus as defined in claim 9, wherein the electrically conductive background body comprises an electrically conductive tubular body.

12. An apparatus as defined in claim 11, wherein the electrodes are mounted to the electrically conductive tubular back-ground body.

13. An apparatus as defined in claim 11, wherein the electrodes are mounted to an electrically insulating tubular support body, the electrically conductive tubular body being supported so as to cover the electrically insulating tubular support body.

14. An apparatus as defined in claim 9, wherein the electrically conductive background body comprises an electrically conductive rod.

15. An apparatus as defined in claim 9, wherein the electrically conductive background body comprises an electrically conductive plate-like body.

16. An apparatus as defined in claim 9, the apparatus further comprising at least one memory, and at least one processor coupled with the at least one memory; wherein the at least one memory comprises program code instructions, which when executed by the at least one processor, cause the apparatus to perform the following steps:
   providing a mathematical model of the target domain determining the electrical quantity of interest for a plurality of pairs of contact element groups;
   adjusting the mathematical model so as to reduce the differences between the measured values of the electrical quantity of interest and those determined by the mathematical model; and
   determining the permittivity on the basis of the adjusted mathematical model.

\* \* \* \* \*